United States Patent
Lai et al.

(10) Patent No.: US 8,124,720 B2
(45) Date of Patent: Feb. 28, 2012

(54) TRIAZINE-BASED MONOMERIC COMPOUND, DI-TRIAZINE COMPOUND, AND DEGRADABLE POLYMER

(75) Inventors: Long-Li Lai, Taichung (TW); Chun-Chi Tseng, Fongyuan (TW); Po-Chung Lin, Taichung (TW); Huey-Fen Tzeng, Taipei (TW); Yi-Lun Chi, Tainan (TW); Tzu-Ping Kuo, Sinjhuang (TW)

(73) Assignee: National Chi Nan University, Puli, Nantou (TW)

( * ) Notice: Subject to any disclaimer, the term of this patent is extended or adjusted under 35 U.S.C. 154(b) by 269 days.

(21) Appl. No.: 12/483,777

(22) Filed: Jun. 12, 2009

(65) Prior Publication Data

US 2009/0312520 A1 Dec. 17, 2009

(30) Foreign Application Priority Data

Jun. 13, 2008 (TW) ................ 97122175 A
Jun. 2, 2009 (TW) ................ 98118186 A

(51) Int. Cl.
*C08G 73/06* (2006.01)
(52) U.S. Cl. .................. 528/423; 544/198
(58) Field of Classification Search .............. None
See application file for complete search history.

(56) References Cited

U.S. PATENT DOCUMENTS

| 3,669,963 A | * | 6/1972 | D'Alelio | 544/194 |
| 3,669,964 A | * | 6/1972 | D'Alelio | 544/194 |
| 5,919,399 A | * | 7/1999 | Gugumus | 252/403 |

FOREIGN PATENT DOCUMENTS

| EP | 0415371 A2 | * | 8/1990 |
| EP | 0 415 371 A2 | | 3/1991 |

OTHER PUBLICATIONS

STIC search Jan. 20, 2011.*

* cited by examiner

*Primary Examiner* — Randy Gulakowski
*Assistant Examiner* — Jeffrey Washville
(74) *Attorney, Agent, or Firm* — Sterne, Kessler, Goldstein & Fox PLLC

(57) ABSTRACT

A triazine-based monomeric compound represented by the following formula (I):

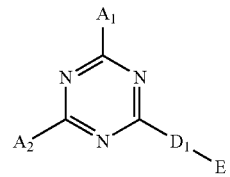

wherein E is H or a substituted triazine group represented by the following formula:

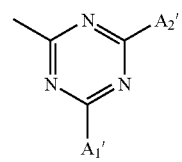

and $D_1$ is represented by the following formula:

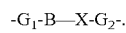

B, X, $G_1$, $G_2$, $A_1$, $A_{1'}$, $A_2$, and $A_{2'}$ are as defined in Claim 1. A di-triazine compound for preparing the triazine-based monomeric compound and a degradable polymer prepared from the triazine-based monomeric compound are also disclosed.

19 Claims, No Drawings

TRIAZINE-BASED MONOMERIC COMPOUND, DI-TRIAZINE COMPOUND, AND DEGRADABLE POLYMER

CROSS-REFERENCE TO RELATED APPLICATION

This application claims priority of Taiwanese Patent application nos. 097122175 and 098118186, filed on Jun. 13, 2008, and Jun. 2, 2009, respectively.

BACKGROUND OF THE INVENTION

1. Field of the Invention

This invention relates to a triazine-based monomeric compound, a di-triazine compound for preparing the triazine-based monomeric compound, and a degradable polymer prepared from the triazine-based monomeric compound.

2. Description of the Related Art

Polymers have been widely used in various industrial fields due to their excellent physical and chemical properties. Because of their enormous consumption worldwide, unavailability of an effective disposal for wasted polymers would inevitably inflict a tremendous impact on the global environment. Therefore, there is a long-felt need to develop an effective way to reduce polymer wastes so as to prevent them from polluting the environment. One means to avoid environmental pollution is to make the polymers degradable.

SUMMARY OF THE INVENTION

Therefore, the object of the present invention is to provide a degradable polymer.

According to one aspect of this invention, there is provided a triazine-based monomeric compound represented by the following formula (I):

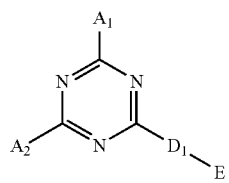
(I)

wherein E is H or a substituted triazine group represented by the following formula:

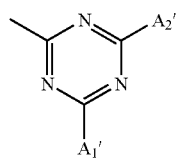

and $D_1$ is represented by the following formula:

-$G_1$-B—X-$G_2$- wherein, when B is a hydrocarbylene group and X is a hydrocarbylene group or a single bond, $G_1$ and $G_2$ are independently N or O; and wherein, when B is a divalent heterocyclic group and X is a hydrocarbylene group or a single bond, $G_1$ and $G_2$ are independently N, O, or a single bond, in which, when B is a divalent heterocyclic group and one of $G_1$ and $G_2$ is a single bond, an atom of the heterocyclic ring of B bonding to the single bond should be a hetero-atom, and in which, when $G_2$ is a single bond, X should be a single bond;

wherein each of $A_1$ and $A_2$ is independently a substituent group, and at least one of $A_1$ and $A_2$ is an active hydrogen-containing group for condensation or addition reaction; and wherein each of $A_{1'}$ and $A_{2'}$ is independently a substituent group, and at least one of $A_{1'}$ and $A_{2'}$ is an active hydrogen-containing group for condensation or addition reaction.

According to another aspect of this invention, there is provided a di-triazine compound for preparing the aforesaid triazine-based monomeric compound. The di-triazine compound is represented by the following formula (II):

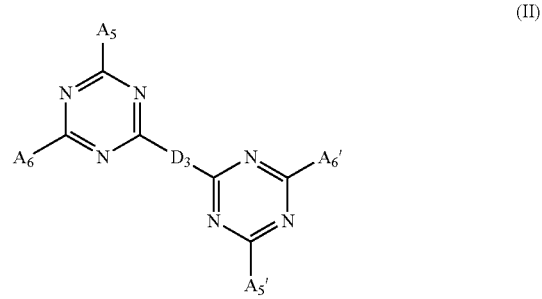
(II)

wherein $D_3$ has the same definition as $D_1$ in formula (I), $A_6$ and $A_{6'}$ are halogen, and $A_5$ and $A_{5'}$ are independently halogen or a substituent group.

According to yet another aspect of this invention, there is provided a degradable polymer prepared by reacting the aforesaid triazine-based monomeric compound with a monomer or a prepolymer which is capable of reacting with the triazine-based monomeric compound by condensation or addition polymerization.

DETAILED DESCRIPTION OF THE PREFERRED EMBODIMENTS

A triazine-based monomeric compound according to the present invention is shown to include a structure of formula (I):

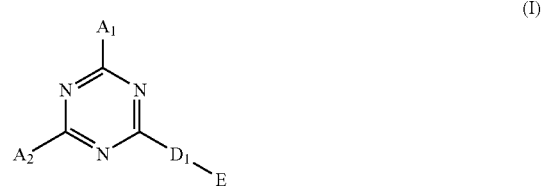
(I)

wherein E is H or a substituted triazine group represented by the following formula:

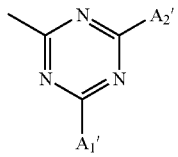

and $D_1$ is represented by the following formula:

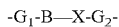

wherein, when B is a hydrocarbylene group and X is a hydrocarbylene group or a single bond, $G_1$ and $G_2$ are independently N or O; and wherein, when B is a divalent heterocyclic group and X is a hydrocarbylene group or a single bond, $G_1$ and $G_2$ are independently N, O, or a single bond, in which, when B is a divalent heterocyclic group and one of $G_1$ and $G_2$ is a single bond, an atom of the heterocyclic ring of B bonding to the single bond should be a hetero-atom, and in which, when $G_2$ is a single bond, X should be a single bond;

wherein each of $A_1$ and $A_2$ is independently a substituent group, and at least one of $A_1$ and $A_2$ is an active hydrogen-containing group for condensation or addition reaction; and wherein each of $A_{1'}$ and $A_{2'}$ is independently a substituent group, and at least one of $A_{1'}$ and $A_{2'}$ is an active hydrogen-containing group for condensation or addition reaction.

Preferably, B is a 1,4-piperazinylene group, a 1,4-piperidylene group, 1,3-cyclohexylene, 1,4-cyclohexylene, meta-phenylene, para-phenylene, or a $C_1$-$C_{20}$ alkylene group.

Preferably, $A_2$ and $A_{2'}$ are independently the active hydrogen-containing group, and $A_1$ and $A_{1'}$ are independently a substituted amino group.

The active hydrogen-containing group is a substituted or non-substituted piperazino group, a hydroxyl piperidino group, or a hydroxyphenyl piperazino group.

Preferably, $A_1$ and $A_{1'}$ are independently

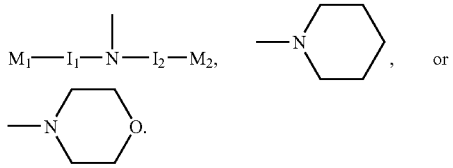

When $I_1$ and $I_2$ are independently a single bond or a $C_1$-$C_{20}$ alkylene group $M_1$ and $M_2$ are independently H, OH,

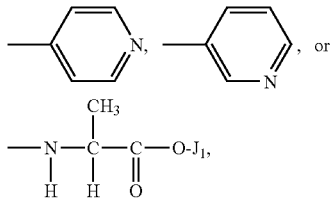

in which $J_1$ is H or a $C_1$-$C_4$ alkyl group. When $I_1$ and $I_2$ are independently a meta-phenylene group or a para-phenylene group, $M_1$ and $M_2$ are independently H, a $C_1$-$C_{20}$ alkyl group, or $OJ_2$, in which $J_2$ is H or a $C_1$-$C_{20}$ alkyl group.

More preferably, $A_1$ and $A_{1'}$ are independently a dibutylamino group, a dihexylamino group, a dioctylamino group, a piperidino group, a morpholinyl group, a diphenylamino group,

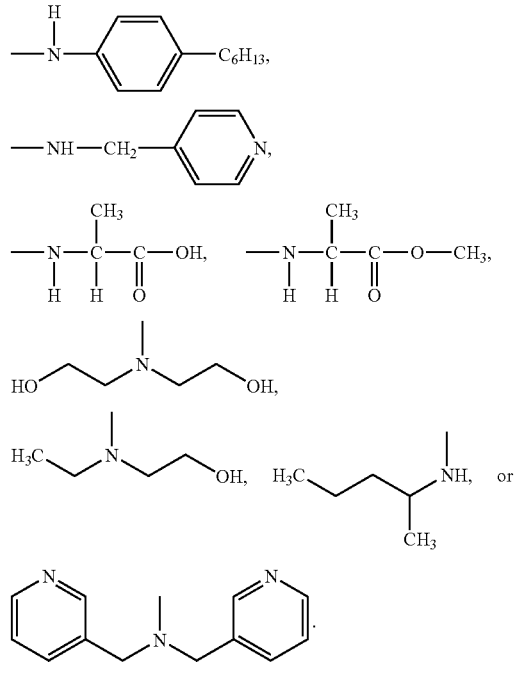

In the Examples of this invention, the substituted amino group is a dibutylamino group, a dihexylamino group, a dioctylamino group, a piperidino group, a morpholinyl group, a diphenylamino group,

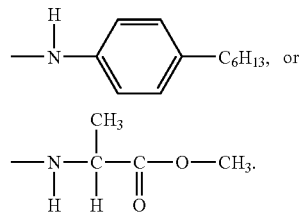

In some examples of this invention, E is a substituted triazine group, $D_1$ is a 1,4-piperazinylene group, $A_1$ and $A_{1'}$ are independently a dibutylamino group, a dihexylamino group, a dioctylamino group, or

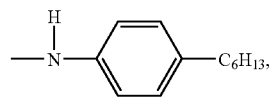

and $A_2$ and $A_{2'}$ are independently a piperazino group, a methyl substituted piperazino group, a hydroxyl piperidino group, or a hydroxyphenyl piperazino group.

In some examples of this invention, E is H, $A_1$ is a dibutylamino group, a dihexylamino group, a dioctylamino group, a piperidino group, a morpholinyl group, a diphenylamino group, or

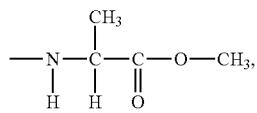

$A_2$ is $D_2H$, and $D_1$ and $D_2$ are independently

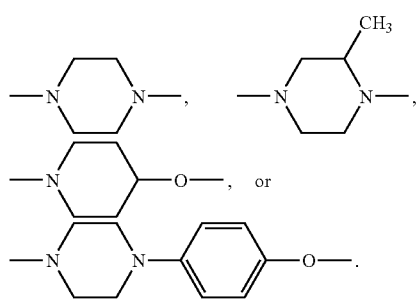

The present invention also discloses a di-triazine compound represented by the following formula (II):

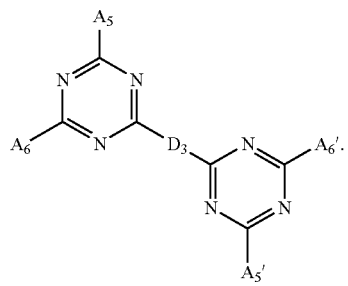

(II)

$D_3$ has the same definition as $D_1$ in formula (I), $A_6$ and $A_{6'}$ are halogen, and $A_5$ and $A_{5'}$ are independently halogen or a substituent group defined as $A_1$ and $A_{1'}$ in formula (I), respectively.

Preferably, the halogen is Cl or Br, and more preferably, is Cl.

Preferably, $D_3$ is 1,4-piperazinylene group.

In an example of this invention, $A_5$, $A_{5'}$, $A_6$, and $A_{6'}$ are Cl.

In some examples of this invention, $A_6$ and $A_{6'}$ are Cl, and $A_5$ and $A_{5'}$ are independently a dibutylamino group, a dihexylamino group, a dioctylamino group, or

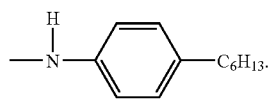

The triazine-based monomeric compound according to the present invention can be used to prepare a degradable polymer. The method includes reacting the triazine-based monomeric compound according to the present invention with a monomer or a prepolymer which is capable of reacting with the triazine-based monomeric compound by condensation or addition polymerization.

The degradable polymer of this invention is represented by the following formula (III):

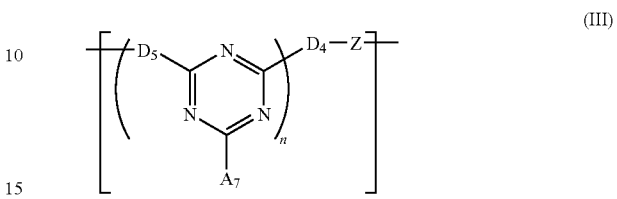

(III)

$D_4$ and $D_5$ has the same definition as $D_1$ in formula (I), and $D_4$ and $D_5$ in each occurrence can be independently the same or different. Z is a divalent group represented by the following formula:

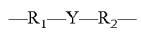

wherein Y is a hydrocarbylene group, and $R_1$ and $R_2$ in each occurrence are independently a bridging group of —CO— or —CO—NH—, so as to form a linkage of —O—CO—, —O—CO—NH—, or

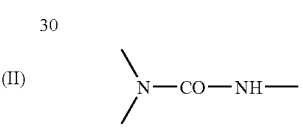

with $D_4$ and $D_5$, respectively. $A_7$ is a substituent group, and n is an integer ranging from 1 to 2.

Preferably, $D_4$ and $D_5$ in each occurrence are independently

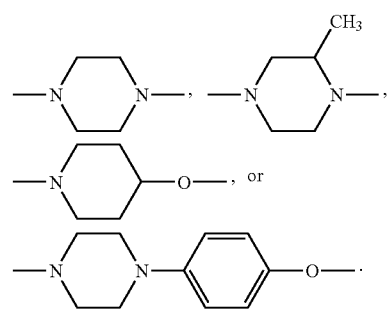

More preferably, $D_4$ and $D_5$ are

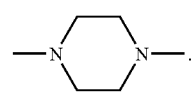

$A_7$ is a substituted amino group and has the same definition as $A_1$ in formula (I). Preferably, $A_7$ is a dibutylamino group, a dihexylamino group, a dioctylamino group, a piperidino group, a morpholinyl group, a diphenylamino group,

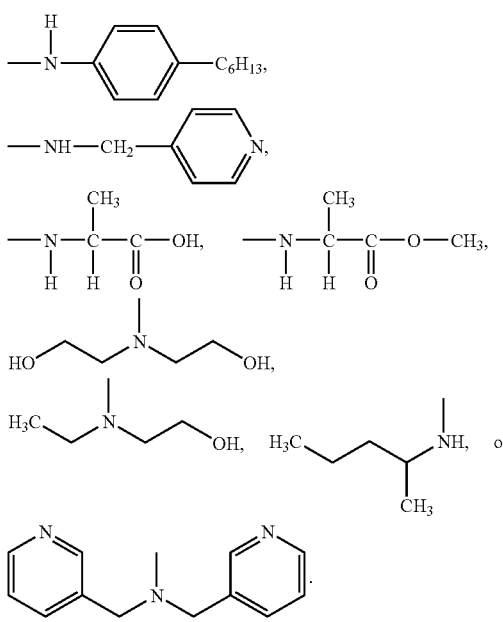

In the experiments of this invention, $A_7$ is —$N(C_4H_9)_2$, —$N(C_6H_{13})_2$, —$N(C_8H_{17})_2$, or

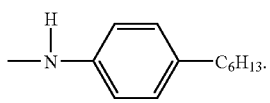

Preferably, Y is an aromatic group. In the experiments of this invention, Y is

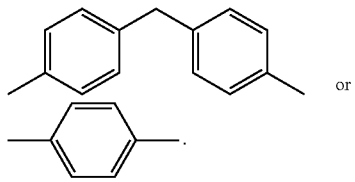

Preferably, the degradable polymer of this invention has a weight average molecular weight ranging from 5,000 to 125,000.

General Preparative Methods

The methods for preparing the compounds of formula (I) and (II) and the degradable polymers of formula (III) are provided below to aid one skilled in the art in synthesizing these compounds and polymers, with more detailed examples in the following Example section.

It should be noted that, preferably, all of the reactions are conducted in the presence of a solvent. The solvent can be any one that is capable of dissolving the reactants, including dichloromethane, tetrahydrofuran (THF), ethanol (EtOH), acetone, acetonitrile, N-methylpyrrolidone, and combinations thereof.

For the sake of convenience, Cl is used as an exemplary example for the halogen group.

The di-triazine compound of formula (II) according to this invention is prepared from cyanuric chloride. Specifically, cyanuric chloride is reacted with a compound having the following formula (R-I) by a substitution reaction:

$$H\text{-}D_3\text{-}H \qquad (R\text{-}I)$$

wherein $D_3$ has the same definition as $D_3$ in formula (II). In the substitution reaction, the reaction temperature is controlled so that only one chlorine atom of each cyanuric chloride is reacted with the compound of (R-I) and two molecules of cyanuric chloride are reacted with one molecule of the compound of formula (R-I) to form the di-triazine compound having the following formula (II-0).

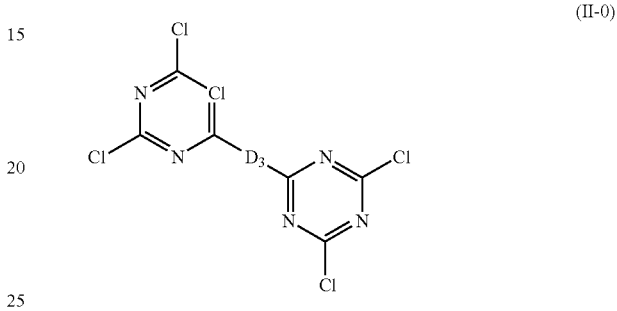

The di-triazine compound of formula (II-0) can be further reacted with a substituted amine, e.g., dibutylamine, dihexylamine, dioctylamine, etc., by substitution reaction to form a di-triazine compound of formula (II), in which $A_5$ and $A_{5'}$ are independently a substituted amino group.

Alternatively, the di-triazine compound of formula (II), in which $A_5$ and $A_{5'}$ are independently a substituted amino group, can be prepared by reacting two mono-substituted cyanuric chloride compounds having the following formulas (e2) and (e3) with the compound of formula (R-I). The reaction temperature should be controlled so that only one chlorine atom of each of the compounds (e2) and (e3) is reacted with the compound of (R-I) and two molecules of cyanuric chloride are reacted with one molecule of the compound of formula (R-I). In the examples of this invention, the reaction temperature ranges from 30 to 60° C., and preferably, from 35 to 55° C. The molar ratio of the mono-substituted cyanuric chloride compounds to the compound of formula (R-I) ranges from 1:0.3 to 1:0.9, and more preferably, from 1:0.49 to 1:0.51. Optionally, during reaction, triethylamine can be added to reduce protonization of nitrogen atom of the mono-substituted cyanuric chloride, thereby resulting in a higher yield.

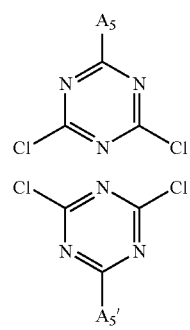

The mono-substituted cyanuric chloride is prepared by reacting cyanuric chloride with a substituted amine compound at a suitable temperature so that only one chlorine atom of each cyanuric chloride is substituted with the substituted amine compound. Preferably, the reaction temperature ranges from −10 to 10° C., and more preferably, from −5 to 5° C. Preferably, the molar ratio of cyanuric chloride to the substituted amine compound ranges from 1:0.7 to 1:1.1, and more preferably, is 1:0.95.

The triazine-based monomeric compound of formula (I), in which E is a substituted triazine group, $A_1$ and $A_{1'}$ are independently a substituted amino group, and $A_2$ and $A_{2'}$ are independently $D_2H$, can be prepared from the di-triazine compound of formula (II), in which $A_5$ and $A_{5'}$ are independently a substituted amino group, and $A_6$ and $A_{6'}$ are Cl. To be specific, the di-triazine compound of formula (II) is reacted with an active hydrogen-containing compound having the following formula (R-II) so that the chlorine atoms of A6 and $A_{6'}$ are substituted by $D_2H$ by a substitution reaction, thereby giving a crude product.

$$H\text{-}D_2\text{-}H \quad\quad (R\text{-}II)$$

Examples of the compound of formula (R-II) include: piperazine, 2-methylpiperazine, piperidinol, and hydroxyphenyl piperazine. In the substitution reaction, the reaction temperature varies based on the reactants. In the examples of this invention, the reaction temperature ranges from 30 to 100° C., and preferably, from 35 to 80° C. When the structure of the compound of formula (R-II) is symmetrical, e.g., piperazine, the molar ratio of the di-triazine compound of formula (II) to the compound of formula (R-II) ranges from 1:5 to 1:7, and preferably, is 1:6. When the structure of the compound of formula (R-II) is asymmetrical, e.g., 2-methylpiperazine or 4-piperidinol, the molar ratio of the di-triazine compound of formula (II) to the compound of formula (R-II) ranges from 1:2 to 1:4, and preferably, from 1:2.4 to 1:3. Preferably, after the substitution reaction, the crude product is then purified. The purification includes the steps of: (1) reacting the crude product with a compound having the following formula (VA) to form a protected compound having the following formula (VB):

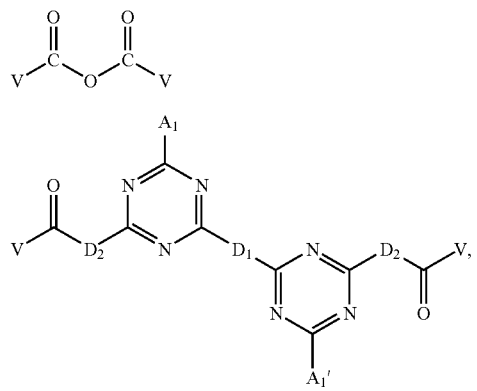

(2) reacting the compound of formula (VB) with a strong base at 20 to 100° C. to remove the protecting group of —VO, thereby giving a purified triazine-based monomeric compound of formula (I). In formulas (VA) and (VB), V is $CF_3$ or $OR_v$, and $OR_v$ is a $C_1$~$C_4$ alkyl group.

Preferably, the compound of formula (VA) is trifluoroacetic anhydride. Preferably, the strong base is KOH or NaOH. Preferably, removal of the protecting group is conducted at 25 to 35° C.

The triazine-based monomeric compound of formula (I), in which E is a substituted triazine group, $A_1$ and $A_{1'}$ are independently a substituted amino group, $A_2$ and $A_{2'}$ are independently $D_2H$, and $D_1$ is identical to $D_2$, can be prepared by (1) reacting the mono-substituted cyanuric chlorides of formulas (e-2) and (e-3) with an excess of the compound of formula (R-I). The reaction temperature is controlled so that one molecule of the compound of formula (R-I) is reacted with one of the chlorine atoms of each of the mono-substituted cyanuric chlorides of formulas (e-2) and (e-3) while the other chlorine atom of each of the mono-substituted cyanuric chlorides of formulas (e-2) and (e-3) is substituted with the compound of formula (R-I). In the examples of this invention, the reaction temperature ranges from 40 to 100° C., and preferably, from 45 to 75° C. The molar ratio of the mono-substituted cyanuric chlorides of formulas (e-2) and (e-3) to the compound of formula (R-I) ranges from 1:4 to 1:6, and preferably, is 1:6. Preferably, the obtained product is then purified to improve the purity of the product, thereby resulting in improvement of the properties of the degradable polymer made therefrom.

The triazine-based monomeric compound of formula (I), in which E is H, $A_1$ is a substituted amino group, $A_2$ is $D_2H$, and $D_1$ is identical to $D_2$, is prepared by reacting a molecule of a mono-substituted cyanuric chloride with two molecules of the compound of formula (R-I) at a suitable temperature. The temperature is varied based on the species of the reactants. In the examples of this invention, the temperature ranges from 30 to 100° C., and preferably, from 35 to 80° C. The molar ratio of the mono-substituted cyanuric chloride to the compound of formula (R-I) ranges from 1:2.0 to 1:4.0, and preferably, from 1:2.2 to 1:2.8. Optionally, during reaction, triethylamine can be added to reduce protonization of nitrogen atom of the mono-substituted cyanuric chloride, thereby resulting in a higher yield.

The degradable polymer according to this invention is prepared by reacting the triazine-based monomeric compound of formula (I) with a monomer or a prepolymer which is capable of reacting with the triazine-based monomeric compound by condensation or addition polymerization.

Preferably, the monomer or the prepolymer has the following formula (IV-1) or formula (IV-2).

$$K=C=N-Y-N=C=K \quad\quad (IV\text{-}1)$$

$$L_3-\overset{O}{\underset{\|}{C}}-Y-\overset{O}{\underset{\|}{C}}-L_4 \quad\quad (IV\text{-}2)$$

In formula (IV-1), Y is as defined in formula (III), and K is 0 or S. Preferably, K is O.

In formula (IV-2), $L_3$ and $L_4$ are independently OH or halogen. Preferably, the halogen is Cl.

Examples of the monomer or prepolymer include, but are not limited to, 4,4'-Diphenylmethane diisocyanate (MDI), para-phenylene diisocyanate (PDI), and those disclosed in U.S. Pat. No. 5,013,770, U.S. Pat. No. 6,503,998, and U.S. Pat. No. 7,378,483.

Preferably, the molar ratio of the triazine-based monomeric compound of formula (I) to a monomer or a prepolymer ranges from 1:0.8 to 1:1.2, and more preferably, is 1:1.

EXAMPLES

Sources of Chemicals
1. Cyanuric chloride: commercially available from ACROS, CAS no. 108-77-0.
2. Dioctylamine: commercially available from ACROS, CAS no. 1120-48-5.
3. Dihexylamine: commercially available from ACROS, CAS no. 143-16-8.
4. Dibutylamine: commercially available from ACROS, CAS no. 111-92-2.
5. Pyridine: commercially available from ACROS, CAS no. 1120-48-5.
6. Diphenylamine: commercially available from Lancaster, CAS no. 122-39-4.
7. 4-Hexylaniline: commercially available from YAKURI, CAS no. 33228-45-4.
8. Morpholine: commercially available from ACROS, CAS no. 110-91-8.
9. Piperazine: commercially available from ACROS, CAS no. 110-85-0.
10. Triethylamine: commercially available from ACROS, CAS no. 121-44-8.
11. Trifluoroacetic anhydride: commercially available from ACROS, CAS no. 407-25-0.
12. 2-methylpiperazine: commercially available from ACROS, CAS no. 109-07-9.
13. 4-piperidinol: commercially available from ACROS, CAS no. 5382-16-1.
14. 1-(4-hydrophenyl)piperazine: commercially available from ACROS, CAS no. 56621-48-8.
15. N-methylpyrrolidone: commercially available from ACROS, CAS no. 872-50-4.
16. 4,4'-Diphenylmethane diisocyanate (MDI): commercially available from ACROS, CAS no. 101-68-8.
17. Para-phenylene diisocyanate (PDI): commercially available from ALDRICH, CAS no. 104-49-4.
18. FBS: commercially available from Biological.
19. Minimal essential medium (MEM): commercially available from GIBCO.
20. 3-(4,5-dimethyl-2-thiazolyl)-2,5-diphenyl-2H-tetrazolium bromide (MTT): commercially available from ACROS, CAS no. 298-93-1.
21. L-alanine methyl ester hydrochloride: commercially available from ACROS, CAS no. 2491-20-5.

General Procedure
1. $^1$H-NMR spectra were obtained using a Bruker AMX300 Solution-NMR spectrometer.
2. Mass spectra were obtained on a JEOL JMS-700 instrument.
3. Elemental analyses were performed on an Elementar Vario EL III instrument.
4. IR spectra were obtained on a Perkin Elmer Spectrum RX spectrometer.
5. The weight loss upon heating and thermo decomposition temperature were measured using Perkin Elmer Pyris 1 TGA.
6. Softening temperature was determined using Perkin Elmer Diamond TMA.
7. Gel permeation chromatography was performed on Ana-Lab Corporation EC 2000.
8. UV-Visible spectra were obtained on a Varian Cary 50 Bio instrument.
9. Cell toxicity (cell compatibility) was measured using a MTT assay.

Preparation of Mono-Substituted Cyanuric Chloride Having the Following Formula

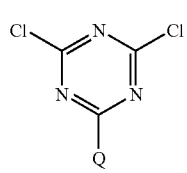

Q = substituted amino group

Preparations 1 to 6

Mono-substituted cyanuric chlorides of Preparations 1 to 6 were prepared using the following steps:

(1) Cyanuric chloride was dissolved in dicholoromethane to give a cyanuric chloride solution.

(2) A substituted amine compound (9 mmol) was dissolved in 10 ml of dicholoromethane to give an amine solution.

(3) To the cyanuric chloride solution, the amine solution was slowly added in an ice bath, thereby forming a first reaction mixture in which a substitution reaction took place. During the substitution reaction, the first reaction mixture was monitored using thin-layer chromatography (TLC) every 10 minutes to determine whether the substitution reaction was complete (i.e., all cyanuric chloride molecules were reacted with the substituted amine compound). After the reaction was complete, the first reaction mixture was washed in an extraction flask with 2 molar equivalents of a potassium carbonate solution.

(4) The combined lower layers (i.e., the organic solvent) were treated with anhydrous magnesium sulfate to remove water from the organic solvent, followed by removal of the magnesium sulfate by filtration and removal of the organic solvent by evaporation at reduced pressure, thereby giving the mono-substituted cyanuric chloride as a white solid.

The amounts of cyanuric chloride and dichloromethane, and the species and the amount of the substituted amine compound for each of Preparations 1 to 6 are shown in Table 1.

TABLE 1

| | Prep. | | | | | |
|---|---|---|---|---|---|---|
| | 1 | 2 | 3 | 4 | 5 | 6 |
| Cyanuric chloride (g/mmol) (g/mmol) | 1.82 g/ 10 mmol | 1.82 g/ 10 mmol | 1.82 g/ 10 mmol | 0.91 g/ 5 mmol | 1.82 g/ 10 mmol | 1.82 g/ 10 mmol |
| $CH_2Cl_2$ for Cyanuric chloride (ml) | 20 | 20 | 20 | 15 | 20 | 20 |
| Substituted amine compound (g) | Dioctyl-amine (2.17 g) | Dihexyl-amine (1.66 g) | Dibutyl-amine (1.16 g) | 4-hexyl-aniline (0.79 g) | Piperidine (0.77 g) | Diphenyl-amine (1.52 g) |

Preparation 7: Preparation of Morpholinyl-Substituted Cyanuric Chloride Having the Following Formula:

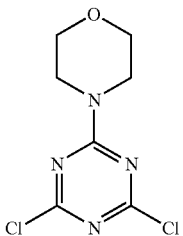

1.00 g (5.4 mmol) of cyanuric chloride was dissolved in 15 ml of acetone, followed by addition of 0.57 g (5.4 mmol) of $Na_2CO_3$, thereby forming a cyanuric chloride mixture. 0.47 g (5.4 mmol) of morpholine was slowly added to the cyanuric chloride mixture in an ice bath to form a reaction mixture. The reaction mixture was allowed to react under stirring in the ice bath, and was monitored by thin-layer chromatography (TLC) every 10 minutes. After the reaction was complete, acetone was removed from the reaction mixture by evaporation at reduced pressure, followed by addition of 20 ml of ice water into the reaction mixture to precipitate the desired product. The white solid product was obtained using filtration, followed by purification using silica column chromatography.

Preparation 8: Preparation of Substituted Cyanuric Chloride Having the Following Formula:

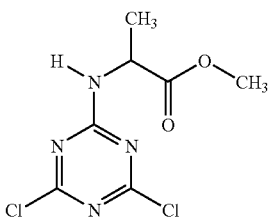

The steps for preparing a substituted cyanuric chloride in Preparation 8 were similar to those of Preparation 1 except that, in step (1), the solvent used for dissolving cyanuric chloride was acetone (20 ml), in step (2), the substituted amine compound was 1.26 g (9 mmol) of L-alanine methyl ester hydrochloride, and the solvent used for dissolving the substituted amine compound was 20 ml of acetone containing 1.38 g (10 mmol) of $K_2CO_3$, and the final product was further purified using silica column chromatography. A purified final product was obtained as a colorless liquid (1.98 g, 82% yield).

Preparation of Substituted Di-Triazine Compound

Preparation of Substituted Di-Triazine Compound Having the Following Formula (II-a)

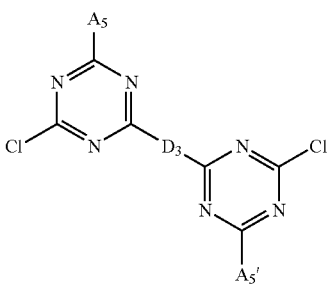

(II-a)

Preparation 9

A substituted di-triazine compound having formula (II-a), in which each of $A_5$ and $A_{5'}$ is $—N(C_8H_{17})_2$, was prepared by the following steps:

(1) 3.88 g (10 mmol) of dioctylamine-substituted cyanuric chloride obtained in Preparation 1 was dissolved in 20 ml of dicholoromethane to form a substituted cyanuric chloride solution.

(2) 0.43 g (5 mmol) of piperazine was dissolved in 10 ml of dicholoromethane to form a piperazine solution.

(3) To the substituted cyanuric chloride solution, the piperazine solution was slowly added, thereby forming a reaction mixture containing hydrochloride salts. The reaction mixture was heated to 40° C. and added with 1.01 g of triethylamine to reduce protonization of nitrogen atom in the triazine ring of the substituted cyanuric chloride by hydrochloride. The reaction mixture was monitored by thin-layer chromatography (TLC). After 12 hours, the reaction mixture was washed twice in an extraction flask with 3 molar equivalents of a potassium carbonate solution.

(4) The combined lower layers (i.e., the organic solvent) of the extracted reaction mixture were treated with anhydrous magnesium sulfate to remove water from the organic solvent, followed by removal of the magnesium sulfate by filtration and removal of the organic solvent by evaporation at reduced pressure, thereby forming a pink solution.

(5) The pink solution was purified by silica column chromatography to obtain a product solution, followed by evaporation at reduced pressure for concentration, thereby giving the desired compound as a colorless liquid (3.08 g, 78% yield).

Structure Identification:

The structure of the substituted di-triazine compound obtained in Preparation 9 was identified using NMR and MASS.

$^1$H-NMR (AMX 300 δ (D-CDCl$_3$)): 0.88 (t, 12H, J=6.6, 4×CH$_3$), 1.29 (S$_{broad}$, 40H, 20×CH$_2$), 1.57 (S$_{broad}$, 8H, 4×CH$_2$), 3.42-3.52 (m, 8H, 4×CH$_3$), 3.82 (S$_{broad}$, 8H, 4×CH$_3$); LRMS calcd for C$_{42}$H$_{77}$Cl$_2$N$_{10}$ (M+H)$^+$: 791.6. Found: 791.4; HRMS calcd for C$_{42}$H$_{77}$Cl$_2$N$_{10}$ (M+H)$^+$: 791.5718. Found: 791.5710.

Preparation 10

The steps for preparing a substituted di-triazine compound in Preparation 10, in which each of $A_5$ and $A_{5'}$ is $—N(C_6H_{13})_2$, were similar to those of Preparation 9. The differences reside in that, in step (1), 3.32 g (10 mmol) of the dihexylamine-substituted cyanuric chloride of Preparation 2 was used to replace 3.88 g (10 mmol) of dioctylamine-substituted cyanuric chloride of Preparation 1, and in step (3), the amount of the potassium carbonate solution was 5 molar equivalents.

Structure Identification:

The structure of the substituted di-triazine compound obtained in Preparation 10 was identified using NMR and MASS. $^1$H-NMR (AMX 300 δ (D-CDCl$_3$)): 0.88 (m, 12H, J=6.6, 4×CH$_3$), 1.29 (S$_{broad}$, 24H, 6×CH$_2$), 1.55 (S$_{broad}$, 8H, 4×CH$_2$), 3.42-3.53 (m, 8H, 4×CH$_2$), 3.81 (S$_{broad}$, 8H, 4×CH$_2$); LRMS calcd for C$_{36}$H$_{61}$Cl$_2$N$_{10}$ (M+H)$^+$: 679.4. Found: 679.3; HRMS calcd for C$_{36}$H$_{61}$Cl$_2$N$_{10}$ (M+H)$^+$: 679.4473. Found: 679.4458.

Preparation 11

The steps for preparing a substituted di-triazine compound in Preparation 11, in which each of $A_5$ and $A_{5'}$ is $—N(C_4H_9)_2$, were similar to those of Preparation 9. The differences reside in that, in step (1), 2.08 g (10 mmol) of the dibutylamine-substituted cyanuric chloride of Preparation 3 was used to replace 3.88 g (10 mmol) of dioctylamine-substituted cyanuric chloride of Preparation 1, and in step (3), the amount of the potassium carbonate solution was 5 molar equivalents. In step (4), the solution obtained after filtration and evaporation at reduced pressure was a pale yellow solution. After chromatography, 2.06 g of a white solid product was obtained.

Structure Identification:

The structure of the substituted di-triazine compound obtained in Preparation 11 was identified using NMR, MASS, and EA. $^1$H-NMR (AMX 300 δ (D-CDCl$_3$)): 0.94 (t, 12H, J=6.6, 4×CH$_3$), 1.36-1.39 (m, 8H, 4×CH$_2$), 1.51-1.62 (m, 8H, 4×CH$_2$), 3.44-3.54 (m, 8H, 4×CH$_2$), 3.81 (S$_{broad}$, 8H, 4×CH$_2$); LRMS calcd for C$_{26}$H$_{45}$Cl$_2$N$_{10}$ (M+H)$^+$: 567. Found: 567; Anal. calcd for C$_{26}$H$_{44}$Cl$_2$N$_{10}$: C 55.02%, H 7.81%, N 24.68%. Found: C 55.02%, H 7.81%, N 24.60%.

Preparation 12

The steps for preparing the substituted di-triazine compound in Preparation 12, in which each of A$_5$ and A$_{5'}$ is —NH(C$_6$H$_6$)C$_6$H$_{13}$, were similar to those of Preparation 8. The differences reside in that, in step (1), 1.62 g (5 mmol) of the 4-hexylaniline-substituted cyanuric chloride of Preparation 4 was used to replace 3.88 g (10 mmol) of dioctylamine-substituted cyanuric chloride of Preparation 1 and the amount of dicholoromethane was 15 ml, and in step (2), the amount of piperazine was 0.215 g (2.5 mmol) and the amount of dicholoromethane for dissolving piperazine was 10 ml. In step (4), the solution obtained after filtration and evaporation at reduced pressure was pale yellow in color. After chromatography, 1.98 g of white solid product was obtained.

Structure Identification:

The structure of the substituted di-triazine compound obtained in Preparation 12 was identified using NMR and MASS. $^1$H-NMR (AMX 300 δ (D-CDCl$_3$)): 0.88 (t, 6H, J=6.3, 2×CH$_3$), 1.31 (S$_{broad}$, 12H, 6×CH$_2$), 1.43 (S$_{broad}$, 4H, 2×CH$_2$), 2.59 (t, 4H, J=7.5, 2×CH$_2$), 3.85~3.97 (mix of triplet, 8H, 4×CH$_2$), 7.17 (d, 4H, J=8.1, 4×CH), 7.42 (d, 4H, J=8.1, 4×CH); LRMS calcd for C$_{34}$H$_{45}$Cl$_2$N$_{10}$ (M+H)$^+$: 663.3. Found: 663.2.

Preparation of Triazine-Based Monomeric Compound Having the Following Formula (I-a)

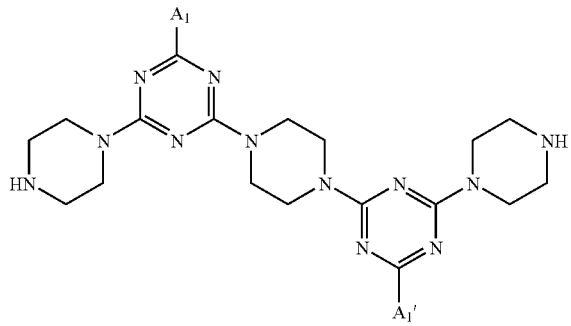

(I-a)

Examples 1-3

Triazine-based monomeric compounds of Examples 1 to 3 having the formula (I-a), in which A$_1$ and A$_{1'}$ are identical and are —N(C$_8$H$_{17}$)$_2$, —N(C$_6$H$_{13}$)$_2$, and —N(C$_4$H$_9$)$_2$ in the Examples 1 to 3, respectively, were prepared by the following steps:

(1) Piperazine was dissolved in ethanol to obtain a piperazine solution.

(2) Amono-substituted cyanuric chloride was dissolved in 20 ml of ethanol to obtain a substituted cyanuric chloride solution.

(3) The substituted cyanuric chloride solution was slowly added into the piperazine solution to form a reaction solution. The reaction solution was allowed to react at 50° C. for 5 hours, followed by adding a large quantity of water and filtration, thereby giving a pale yellow solid. The pale yellow solid was dissolved in dichloromethane, followed by addition of anhydrous magnesium sulfate to remove water.

(4) The magnesium sulfate was removed by filtration and the solvent was removed by evaporation at reduced pressure, thereby giving a crude extract. The crude extract was then dissolved in dichloromethane to give a crude extract solution.

(5) Trifluoroacetic anhydride was dissolved in dichloromethane, thereby giving a trifluoroacetic anhydride solution, followed by slow addition of the trifluoroacetic anhydride solution into the crude extract solution in an ice bath to form a reaction mixture. The reaction mixture was allowed to react in the ice bath for 30 minutes and at room temperature for 9.5 hours.

(6) The reaction mixture was washed with 5 molar equivalents of a potassium carbonate solution. The combined lower layers (i.e., the organic solvent) of the extracted reaction mixture were treated with anhydrous magnesium sulfate to remove water from the organic solvent. The solid magnesium sulfate was removed from the organic solvent by filtration, followed by evaporation at reduced pressure, thereby giving an intermediate as a pale yellow solid.

(7) The pale yellow intermediate was purified using silicon column chromatography, followed by evaporation at reduced pressure, thereby giving 3.02 g of pure intermediate compound. The pure intermediate compound was identified using NMR, MASS, and EA, and has the following formula:

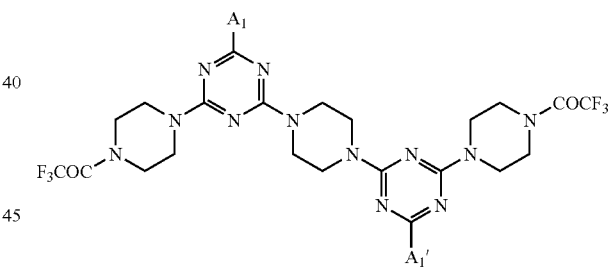

(8) Steps (1) to (7) were repeated to obtain sufficient amount of the pure intermediate compound.

(9) The pure intermediate compound was dissolved in a solution containing 20 ml of ethanol, 2.5 ml of dichloromethane, and 2.5 ml of water, followed by reaction with potassium hydroxide for 1 hour. The reaction solution was evaporated at reduced pressure, and then was added with a large quantity of water, followed by stirring for 1 hour and then filtration, thereby giving a final product as a white solid.

The species and/or the amounts of the reactants and the amounts of the solvents for Examples 1 to 3 are shown in Table 2. The structure of the final product obtained in each of Examples 1 to 3 was identified using NMR, MASS, and/or EA. The results are shown below.

Example 1

$^1$H-NMR (AMX300 δ (D-CDCl$_3$)): 0.87 (t, 12H, J=6.6, 4×CH$_3$), 1.28 (S$_{broad}$, 40H, 20×CH$_2$), 1.55 (S$_{broad}$, 8H, 4×CH$_2$), 2.88 (S$_{broad}$, 8H, 4×CH$_2$), 3.46 (S$_{broad}$, 8H, 4×CH$_2$), 3.76 (S$_{broad}$, 16H, 8×CH$_2$); LRMS calcd for C$_{50}$H$_{95}$N$_{14}$ (M+H)$^+$: 891.8. Found: 891.7; Anal. calcd for C$_{50}$H$_{94}$N$_{14}$: C 67.37%, H 10.63%, N 22.00%. Found: C 67.30%, H 10.68%, N 21.97%.

Example 2

$^1$H-NMR (AMX300 δ (D-CDCl$_3$)): 0.84 (t, 12H, J=6.6, 4×CH$_3$), 1.25 (S$_{broad}$, 24H, 12×CH$_2$), 1.52 (S$_{broad}$, 8H, 4×CH$_2$), 2.83 (t, 8H, J=5.1, 4×CH$_2$), 3.42 (t, 8H, J=7.2, 4×CH$_2$), 3.69 (t, 16H, J=5.1, 8×CH$_2$); LRMS calcd for: C$_{42}$H$_{79}$N$_{14}$ (M+H)$^+$: 779.7. Found: 779.6; Anal. calcd for C$_{42}$H$_{78}$N$_{14}$: C 64.74%, H 10.09%, N 25.17%. Found: C 66.46%, H 10.05%, N 25.07%.

Example 3

$^1$H-NMR (AMX 300 δ (D-CDCl$_3$)): 0.89 (t, 12H, J=6.6, 4×CH$_3$), 1.23-1.35 (m, 8H, 4×CH$_2$), 1.48-1.59 (m, 8H, 4×CH$_2$), 2.83 (t, 8H, J=5.1, 4×CH$_2$), 3.44 (t, 8H, J=7.2, 4×CH$_2$), 3.72 (t, 16H, J=5.1, 8×CH$_2$); LRMS calcd for C$_{36}$H$_{63}$N$_{14}$ (M+H)$^+$: 667.5. Found: 667.5.

Example 4

The steps for preparing a triazine-based monomeric compound in Example 4, in which A$_1$ and A$_{1'}$ are —NH(C$_6$H$_6$)C$_6$H$_{13}$, were similar to those of Example 1 except for the species and/or the amounts of the reactants and the amounts of the solvents, and the operation procedure in step (9). The species and/or the amounts of the reactants and the solvents are shown in Table 2. The differences in step (9) reside in that, after reacting with potassium hydroxide, the reaction solution was evaporated at reduced pressure and then added with dichloromethane, followed by washing twice with 5 molar equivalents of a potassium carbonate solution. The combined lower layers (i.e., the organic solvent) of the extracted solution were treated with anhydrous magnesium sulfate to remove water from the organic solvent. The solid magnesium sulfate was removed from the organic solvent by filtration, followed by evaporation of the organic solvent at reduced pressure, thereby yielding the final product.

Structure Identification:

The structure of the final product obtained in Example 4 was identified using NMR and MASS. $^1$H-NMR (AMX 300 δ (D-CDCl$_3$)): 0.87 (t, 6H, J=6.6, 2×CH$_3$), 1.29 (S$_{broad}$, 12H, 6×CH$_2$), 1.53-1.60 (m, 4H, 2×CH$_2$), 2.55 (t, 4H, J=7.2, 2×CH$_2$), 2.89 (t, 8H, J=5.1, 4×CH$_2$), 3.77 (t, 16H, J=5.1, 8×CH$_2$), 6.70 (s, 2H, 2×NH), 7.11 (d, 4H, J=8.4, 4×CH), 7.46 (d, 4H, J=8.4, 4×CH); LRMS calcd for C$_{42}$H$_{63}$N$_{14}$ (M+H)$^+$: 763.5. Found: 763.5.

TABLE 2

| | Example | | | |
|---|---|---|---|---|
| | 1 | 2 | 3 | 4 |
| Piperazine (g/mmol) | 4.3 g/ 50 mmol | 2.15 g/ 25 mmol | 2.15 g/ 25 mmol | 2.15 g/ 25 mmol |
| Ethanol (ml) | 80 | 50 | 50 | 50 |
| Mono-substituted cyanuric chloride (g/mmol) | Prep. 1 3.88 g/ 10 mmol | Prep. 2 1.66 g/ 5 mmol | Prep. 3 1.04 g/ 5 mmol | Prep. 4 1.62 g/ 5 mmol |
| Dichloromethane in step (3) (ml) | 40 | 30 | 30 | 30 |
| Trifluoroacetic anhydride (g/mmol) | 4.2 g/ 20 mmol | 2.73 g/ 13 mmol | 2.73 g/ 13 mmol | 2.73 g/ 13 mmol |
| Dichloromethane in step (5) (ml) | 15 | 10 | 10 | 10 |
| Pure intermediate compound used in step (9) (g/mmol) | 5.41 g/ 5 mmol | 4.58 g/ 5 mmol | 4.29 g/ 5 mmol | 4.77 g/ 5 mmol |
| Potassium hydroxide in step (9) (g/mmol) | 1.95 g/ 30 mmol | 1.96 g/ 35 mmol | 1.96 g/ 35 mmol | 1.96 g/ 35 mmol |
| Final product (g) | 4.13 | 3.62 | 3.19 | 3.28 |
| Yield (%) | 93 | 92 | 96 | 86 |

Examples 5 to 8

The triazine-based monomeric compounds of Examples 5 to 8 having the chemical structure formulas identical to those of Examples 1 to 4 can be prepared from the substituted di-triazine compounds obtained in preparations 9 to 12, respectively, using the following procedures:

(1) Each of the substituted di-triazine compounds obtained in Preparations 9 to 12 was dissolved in THF to obtain a di-triazine solution.

(2) 2.58 g (30 mmol) of Piperazine was dissolved in THF to obtain a piperazine solution. The piperazine solution was slowly added into the di-triazine solution to form a reaction mixture.

(3) The reaction mixture was allowed to react at 50° C., and was monitored by thin-layer chromatography (TLC). After the reaction was complete, the reaction mixture was extracted twice in an extraction flask using a potassium carbonate solution. The combined lower layers (i.e., the organic solvent) of the extracted reaction mixture were treated with anhydrous magnesium sulfate to remove water from the organic solvent. The solid magnesium sulfate was removed from the organic solvent by filtration, followed by evaporation at reduced pressure, thereby yielding a final product.

The species and amounts of the reactants and solvents for preparing the triazine-based monomeric compounds of Examples 1 to 4 from the substituted di-triazine compounds are shown in Table 3.

TABLE 3

| | Example | | | |
|---|---|---|---|---|
| | 5 | 6 | 7 | 8 |
| Substituted di-triazine compound (g/mmol) | Prep. 9 3.95 g/ 5 mmol | Prep. 10 3.32 g/ 5 mmol | Prep. 11 2.83 g/ 5 mmol | Prep. 12 3.31 g/ 5 mmol |
| THF in step (1) (ml) | 15 | 10 | 10 | 20 |
| THF in step (2) (ml) | 30 | 20 | 20 | 25 |
| Final product (g) | 4.23 | 3.73 | 3.18 | 3.41 |
| Yield (%) | 95 | 96 | 96 | 91 |

Structure Identification:

The structures of the triazine-based monomeric compounds obtained in Examples 5 to 8 were identified using NMR. The NMR results of Examples 5 to 8 were the same as those of Examples 1 to 4, respectively.

The crude extracts obtained in step (4) of Examples 1 to 4 and the final products obtained in Examples 1 to 8 were identified using FT-IR. The FT-IR results show that, in all spectra of the crude extracts and the final products, an N—H absorbance peak was observed between 3100 to 3400 cm$^{-1}$. In the spectra for all of the final products, C═N absorbance peak was observed at 1430 to 1545 cm$^{-1}$. In the spectra for the final products of Examples 4 and 8, C═C absorbance peak was observed at 1610 cm$^{-1}$. The FT-IR results are consistent with the NMR results.

Preparation of Triazine-Based Monomeric Compound Having the Following Formula (I-b)

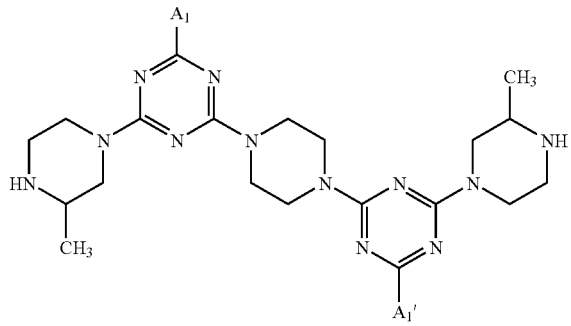

Example 9

A triazine-based monomeric compound having the formula (I-b), in which $A_1$ and $A_{1'}$ are —N($C_8H_{17}$)$_2$, was prepared by the following steps:

(1) 6.34 g (8 mmol) of the substituted di-triazine compounds obtained in Preparation 9 was dissolved in 20 ml THF to obtain a di-triazine solution.

(2) 1.25 g (20 mmol) of 2-methylpiperazine was dissolved in 20 ml THF to obtain a 2-methylpiperazine solution. The 2-methylpiperazine solution was slowly added into the di-triazine solution to form a reaction mixture.

(3) The reaction mixture was heated to 40° C., and added with 2.42 g (22 mmol) of triethylamine. The reaction mixture was reacted at reflux temperature, and was monitored by thin-layer chromatography (TLC). After the reaction was complete, the reaction mixture was evaporated at reduced pressure to remove THF, dissolved in dichloromethane, and then washed with 5 molar equivalents of potassium carbonate solution. The lower layers (i.e., the organic solvent layers) of the extracted reaction mixture were treated with anhydrous magnesium sulfate to remove water from the organic solvent. The solid magnesium sulfate was removed from the organic solvent by filtration, followed by evaporation at reduced pressure, thereby giving 6.32 g of final product. The yield was 86%.

Structure Identification:

The structure of the final product was identified using NMR and MASS. $^1$H-NMR (AMX 300 δ (D-CDCl$_3$)): 0.87 (t, 12H, J=6.3, 4×CH$_3$), 1.08 (d, 6H, J=5.7, 2×CH$_3$), 1.25-1.29 (m, 40H, 20×CH$_2$), 1.50-1.60 (m, 10H, 4×CH$_2$, 2×NH), 2.38-2.43 (m, 2H, 1×CH$_2$), 2.72-2.84 (m, 6H, 2×CH, 2×CH$_2$), 2.96-3.05 (m, 2H, 1×CH$_2$), 3.46 (t, 8H, J=7.5, 4×CH$_2$), 3.75-3.83 (m, 8H, 4×CH$_2$), 4.55-4.65 (m, 4H, 2×CH$_2$); LRMS calcd for C$_{52}$H$_{98}$N$_{14}$ (M+H)$^+$: 920. Found: 920.

Example 10

The steps for preparing a triazine-based monomeric compound in Example 10, in which $A_1$ and $A_{1'}$ are —N(C$_6$H$_{13}$)$_2$, were similar to those of Example 9 except for the species and/or the amounts of the reactants and the species and/or the amounts of the solvents. The differences are shown in Table 4.

Structure Identification:

The structure of the final product was identified using NMR and MASS. $^1$H-NMR (AMX 300 δ (D-CDCl$_3$)): 0.88 (t, 12H, J=6.2, 4×CH$_3$), 1.08 (d, 6H, J=6.2, 2×CH$_3$), 1.22-1.35 (m, 24H, 12×CH$_2$), 1.50-1.60 (m, 10H, 4×CH$_2$, 2×NH), 2.37-2.48 (m, 2H, 1×CH$_2$), 2.70-2.86 (m, 6H, 2×CH, 2×CH$_2$), 2.93-3.05 (m, 2H, 1×CH$_2$), 3.46 (t, 8H, J=7.4, 4×CH$_2$), 3.74-3.80 (m, 8H, 4×CH$_2$), 4.54-4.68 (m, 4H, 2×CH$_2$); LRMS calcd for C$_{44}$H$_{82}$N$_{14}$ (M+H)$^+$: 807. Found: 807.

Example 11

The steps for preparing a triazine-based monomeric compound in Example 11, in which $A_1$ and $A_{1'}$ are —N(C$_4$H$_9$)$_2$, were similar to those of Example 9 except for the species and/or the amounts of the reactants and the species and/or the amounts of the solvents. The differences are shown in Table 4.

Structure Identification:

The structure of the final product was identified using NMR and MASS. $^1$H-NMR (AMX 300 δ (D-CDCl$_3$)): 0.93 (t, 12H, J=7.5, 4×CH$_3$), 1.08 (d, 6H, J=6.3, 2×CH$_3$), 1.28-1.3 (m, 8H, 4×CH$_2$), 1.50-1.65 (m, 10H, 4×CH$_2$, 2×NH), 2.35-2.50 (m, 2H, 1×CH$_2$), 2.70-2.85 (m, 6H, 2×CH, 2×CH$_2$), 2.95-3.05 (m, 2H, 1×CH$_2$), 3.48 (t, 8H, J=7.3, 4×CH$_2$), 3.77 (s, 8H, 4×CH$_2$) 4.52-4.63 (m, 4H, 2×CH$_2$); LRMS calcd for C$_{36}$H$_{66}$N$_{14}$ (M+H)$^+$: 695. Found: 695.

Preparation of Triazine-Based Monomeric Compound Having the Following Formula (I-c)

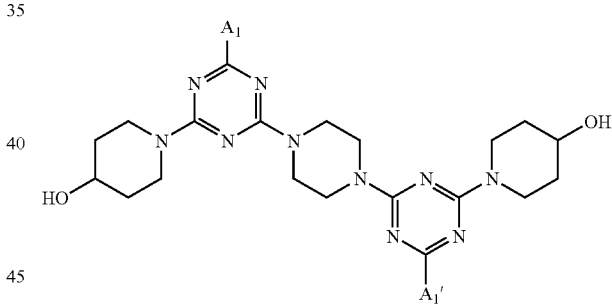

Examples 12 to 14

The steps for preparing triazine-based monomeric compounds in Examples 12 to 14, in which $A_1$ and $A_{1'}$ are identical and are —N(C$_8$H$_{17}$)$_2$, —N(C6H$_{13}$)$_2$, and —N(C$_4$H$_9$)$_2$, respectively in Examples 12 to 14, were similar to those of Example 9 except for the species and the amounts of the reactants, the species and/or the amounts of the solvents, and the reaction temperature. The differences are shown in Table 4. The structure of each of the final products in Examples 12 to 14 was identified using NMR, MASS, and/or EA. The results are shown below.

Example 12

$^1$H-NMR (AMX 300 δ (D-CDCl$_3$)): 0.88 (t, 12H, J=6.9, 4×CH$_3$), 1.26-1.30 (m, 40H, 20×CH$_2$), 1.40-1.60 (m, 14H, 6×CH$_2$, 2×OH), 1.86-193 (m, 4H, 2×CH$_2$), 3.11-3.20 (m, 4H, 2×CH$_2$), 3.47 (t, 4H, J=7.3, 2×CH$_2$), 3.78 (s, 8H, 4×CH$_2$), 3.85-3.90 (m, 2H, 2×CH), 3.38-4.46 (m, 4H, 2×CH$_2$); LRMS calcd for C$_{52}$H$_{96}$N$_{12}$O$_2$ (M+H)$^+$: 921. Found: 921; Anal. calcd for C$_{52}$H$_{95}$N$_{12}$O$_2$: C 67.78%, H 10.50%, N 18.24%. Found: C 67.71%, H 10.51%, N 18.21%.

Example 13

$^1$H-NMR (AMX 300 δ (D-CDCl$_3$)): 0.89 (t, 12H, J=6.3, 4×CH$_3$), 1.28-1.32 (m, 24H, 12×CH$_2$), 1.46-1.60 (m, 14H, 6×CH$_2$, 2×OH), 1.87-1.93 (m, 4H, 2×CH$_2$), 3.10-3.20 (m, 4H, 2×CH$_2$), 3.40-3.50 (t, 8H, J=7.2, 4×CH$_2$), 3.78 (s, 8H, 4×CH$_2$), 3.85-3.90 (m, 2H, 2×CH), 4.38-4.63 (m, 4H, 2×CH$_2$); LRMS calcd for C$_{44}$H$_{80}$N$_{12}$O$_2$ (M+H)$^+$: 809. Found: 809; Anal. calcd for C$_{44}$H$_{79}$N$_{12}$O$_2$: C 65.31%, H 9.96%, N20.77%. Found: C 64.99%, H 9.92%, N 20.72%.

Example 14

$^1$H-NMR (AMX 300 δ (D-CDCl$_3$)): 0.93 (t, 12H, J=7.2, 4×CH$_3$), 1.28-1.35 (m, 8H, 4×CH$_2$), 1.50-1.60 (m, 14H, 6×CH$_2$, 2×OH), 1.80-1.94 (m, 4H, 2×CH$_2$), 3.10-3.20 (m, 4H, 2×CH$_2$), 3.45-3.50 (t, 4H, J=7.5, 2×CH$_2$), 3.77 (s, 8H, 4×CH$_2$), 3.85-3.90 (m, 2H, 2×CH), 4.38-4.45 (m, 4H, 2×CH$_2$); LRMS calcd for C$_{36}$H$_{64}$N$_{12}$O$_2$(M+H)$^+$: 697. Found: 697; Anal. calcd for C$_{36}$H$_{63}$N$_{12}$O$_2$: C 62.04%, H 9.26%, N 24.12%. Found: C 62.12%, H 9.26%, N 24.19%.

(2) 2-Methylpiperazine was dissolved in THF to obtain a 2-methylpiperazine solution. The 2-methylpiperazine solution was slowly added into the cyanuric chloride solution to form a reaction mixture.

(3) The reaction mixture was heated to 40° C., and added with triethylamine. The reaction mixture was then reacted at reflux temperature, and was monitored using thin-layer chromatography (TLC). After the reaction was complete, THF was removed using evaporation at reduced pressure. The reaction mixture was then dissolved in dichloromethane and washed with 5 molar equivalents of a potassium carbonate solution. The combined lower layers (i.e., the organic solvent) of the extracted reaction mixture were washed twice with water, followed by addition of anhydrous magnesium sulfate to remove water from the organic solvent. The solid magnesium sulfate was removed from the organic solvent by filtration, followed by evaporation at reduced pressure and silica column chromatography, thereby yielding a final product.

Examples 15-21

The triazine-based monomeric compounds in Examples 15 to 21, in which A$_1$ are —N(C$_8$H$_{17}$)$_2$, —N(C$_6$H$_{13}$)$_2$, —N(C$_4$H$_9$)$_2$, —NC$_5$H$_{10}$, morpholinyl, diphenylamino, and

TABLE 4

| | Example | | | | | |
|---|---|---|---|---|---|---|
| | 9 | 10 | 11 | 12 | 13 | 14 |
| Solute in step (1) (g/mmol) | Prep. 9 6.34 g/ 8 mmol | Prep. 10 3.34 g/ 5 mmol | Prep. 11 2.83 g/ 5 mmol | Prep. 9 1.58 g/ 2 mmol | Prep. 10 3.35 g/ 5 mmol | Prep. 11 1.16 g/ 2 mmol |
| THF in step (1) (ml) | 20 | 15 | 15 | 10 | 20 | 10 |
| Solute in Step (2) (g/mmol) | 2-methyl piperazine 1.25 g/ 20 mmol | 2-methyl piperazine 1.20 g/ 12 mmol | 2-methyl piperazine 1.20 g/ 12 mmol | 4-piperidinol 0.60 g/ 6 mmol | 4-piperidinol 1.57 g/ 15 mmol | 4-piperidinol 0.60 g/ 6 mmol |
| THF in Step (2) (ml) | 20 | 15 | 20 | 10 | 20 | 10 |
| Temperature in Step (3) | 40 | 40 | 40 | 50 | 50 | 40 |
| Triethylamine in Step (3) (g/mmol) | 2.42 g/ 22 mmol | 1.32 g/ 12 mmol | 2.42 g/ 22 mmol | 0.61 g/ 6 mmol | 1.52 g/ 15 mmol | 2.24 g/ 22 mmol |
| Final product (g) | 6.32 | 3.15 | 3.05 | 1.68 | 3.62 | 1.30 |
| Yield (%) | 86 | 78 | 88 | 91 | 89 | 93 |

Preparation of Triazine-Based Monomeric Compound Having the Following Formula (I-d)

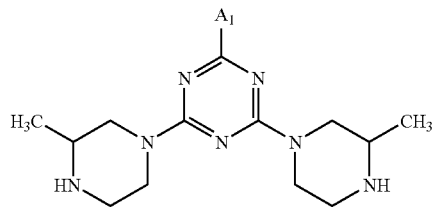

(I-d)

Preparation Step:

(1) Mono-substituted cyanuric chloride obtained in each of Preparations 1 to 3 and 5 to 8 was dissolved in THF to obtain a cyanuric chloride solution.

$$-N-\overset{\overset{\displaystyle CH_3}{|}}{\underset{\underset{\displaystyle H}{|}}{C}}-\overset{\overset{\displaystyle}{|}}{\underset{\underset{\displaystyle H}{|}}{C}}-O-CH_3;$$

respectively, were prepared using the aforesaid preparation method. The species and the amounts of the reactants and the amounts of THF for Examples 15 to 21 are shown in Table 5. The structure of each of the final products in Examples 15 to 21 was identified using NMR and MASS. The results are shown below.

Example 15

$^1$H-NMR (AMX 300 δ (D-CDCl$_3$)): 0.87 (t, 6H, J=6.9, 2×CH$_3$), 1.08 (d, 6H, J=6.3, 2×CH$_3$), 1.25-1.28 (m, 20H, 10×CH$_2$), 1.50-1.60 (m, 6H, 2×CH$_2$, 2×NH), 2.35-0.247 (m, 2H, 2×CH$_2$), 2.72-2.84 (m, 6H, 2×CH, 2×CH$_2$), 2.95-3.05 (m, 2H, 1×CH$_2$), 3.44 (t, 4H, J=7.5, 2×CH$_2$), 4.45-4.60 (m, 4H, 2×CH$_2$); LRMS calcd for C$_{29}$H$_{56}$N$_8$(M+H)$^+$: 517. Found: 517.

Example 16

$^1$H-NMR (AMX 300 δ (D-CDCl$_3$)): 0.86 (t, 6H, J=6.3, 2×CH$_3$), 1.08 (d, 6H, J=6.0, 2×CH$_3$), 1.26-1.29 (m, 12H, 6×CH$_2$), 1.55-1.68 (m, 6H, 2×CH$_2$, 2×NH), 2.36-2.50 (m, 2H, 1×CH$_2$), 2.72-2.84 (m, 6H, 2×CH, 2×CH$_2$), 2.95-3.01 (m, 2H, 2×CH$_2$), 3.44 (t, 4H, J=7.5, 2×CH$_2$), 4.55-4.64 (m, 4H, 2×CH$_2$); LRMS calcd for C$_{25}$H$_{48}$N$_8$ (M+H)$^+$: 461. Found: 461.

Example 17

$^1$H-NMR (AMX 300 δ (D-CDCl$_3$)): 0.92 (t, 6H, J=7.2, 2×CH$_3$), 1.08 (d, 6H, J=6.3, 2×CH$_3$), 1.30 (m, 4H, 2×CH$_2$), 1.50-1.65 (m, 6H, 2×CH$_2$, 2×NH), 2.38-2.48 (m, 2H, 1×CH$_2$), 2.70-2.85 (m, 6H, 2×CH, 2×CH$_2$), 2.95-3.05 (m, 2H, 1×CH$_2$), 3.44 (t, 4H, J=7.8, 2×CH$_2$), 4.55-4.65 (m, 4H, 2×CH$_2$); LRMS calcd for C$_{21}$H$_{40}$N$_8$ (M+H)$^+$: 405. Found: 405.

Example 18

$^1$H-NMR (AMX 300 δ (D-CDCl$_3$)) 1.09 (d, 6H, J=6.3, 2×CH$_3$), 1.50-1.70 (m, 8H, 3×CH$_2$, 2×NH), 2.35-2.48 (m, 2H, 1×CH$_2$), 2.72-2.84 (m, 6H, 2×CH, 2×CH$_2$), 2.95-3.05 (m, 2H, 1×CH$_2$), 3.70 (t, 4H, J=5.5, 2×CH$_2$), 4.43-4.65 (m, 4H, 2×CH$_2$); LRMS calcd for C$_{18}$H$_{32}$N$_8$ (M+H)$^+$: 361. Found: 361.

Example 19

$^1$H-NMR (AMX 300 δ (D-CDCl$_3$)): 1.09 (d, 6H, J=6.2, 2×CH$_3$), 1.89 (s, 2H, 2×NH), 2.40-2.50 (m, 2H, 1×CH$_2$), 2.72-2.84 (m, 6H, 2×CH, 2×CH$_2$), 2.95-3.05 (m, 2H, 1×CH$_2$), 3.68-3.76 (m, 8H, 4×CH$_2$), 4.43-4.65 (m, 4H, 2×CH$_2$); LRMS calcd for C$_{17}$H$_{30}$N$_8$O (M+H)$^+$: 363. Found: 363.

Example 20

$^1$H-NMR (AMX 300 δ (D-CDCl$_3$)): 1.09 (d, 6H, J=6.2, 2×CH$_3$), 1.56 (s, 2H, 2×NH), 2.30-2.45 (M, 2H, 1×CH$_2$), 2.72-2.84 (m, 6H, 2×CH, 2×CH$_2$), 2.95-3.05 (m, 2H, 1×CH$_2$), 4.43-4.65 (m, 4H, 2×CH$_2$), 7.08-7.14 (m, 2H, 2×CH) 7.22-7.28 (m, 8H, 8×CH); LRMS calcd for C$_{25}$H$_{32}$N$_8$ (M+H)$^+$: 445. Found: 445.

Example 21

$^1$H NMR (300 MHz CDCl$_3$·δ, ppm) 1.08 (d, 6H, J=6.0, 2×CH$_3$), 1.42 (d, 3H, J=7.2 1×CH$_3$), 2.35-2.48 (m, 2H, 1×CH$_2$), 2.70-2.82 (m, 6H, 2×CH$_2$, 2×CH), 2.95-3.05 (m, 2H, 1×CH$_2$), 3.70 (s, 3H, 1×CH$_3$), 4.45-4.65 (m, 5H, 2×CH$_2$, 1×CH), 5.09 (d, 1H, J=6.9, 1×NH); $^{13}$C NMR (CDCl$_3$·δ, ppm): 18.6 (C$^3$), 19.6 (C$^9$), 43.4 (C$^{11}$), 45.8 (C$^{10}$), 49.6 (C$^1$), 50.4 (C$^7$), 50.5 (C$^8$), 51.9 (C$^4$), 128.0 (C$^3$), 164.9 (C$^5$), 165.5 (C$^6$), 174.6 (C$^2$); LRMS calcd for C$_{17}$H$_{30}$N$_8$O$_2$ (M+H)$^+$: 379. Found: 379.

TABLE 5

|  | Example | | | | | | |
| --- | --- | --- | --- | --- | --- | --- | --- |
|  | 15 | 16 | 17 | 18 | 19 | 20 | 21 |
| Mono-substituted cyanuric chloride (g) | Prep. 1 3.89 g | Prep. 2 3.33 g | Prep. 3 2.77 g | Prep. 5 2.33 g | Prep. 7 2.35 g | Prep. 6 0.32 g | Prep. 8 0.32 g |
| THF in step (1) (ml) | 20 | 20 | 20 | 20 | 20 | 5 | 10 |
| 2-Methyl-piperazine (g) | 2.20 g | 2.20 g | 2.20 g | 2.20 g | 2.20 g | 0.30 g | 0.81 g |
| THF in step (2) (ml) | 20 | 20 | 20 | 20 | 20 | 5 | 10 |
| Triethylamine in step (3) (g) | 2.24 g | 2.24 g | 2.24 g | 2.24 g | 2.24 g | 0.33 g | 0.88 g |
| Final product (g) | 4.65 g | 4.15 g | 3.72 g | 3.06 g | 3.26 g | 0.36 g | 0.86 g |
| Yield (%) | 90 | 91 | 92 | 85 | 90 | 81 | 76 |

Preparation of Triazine-Based Monomeric Compound Having the Following Formula (I-e)

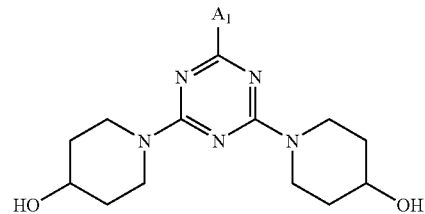

(I-e)

Examples 22-24

The steps for preparing the triazine-based monomeric compounds in Examples 22 to 24, in which A$_1$ are —N(C$_8$H$_{17}$)$_2$, —N(C$_6$H$_{13}$)$_2$, and —N(C$_4$H$_9$)$_2$, respectively, were similar to those for preparing the triazine-based monomeric compound of formula (I-d) except for the species and the amounts of the reactants and the solvents. In addition, in Examples 22 to 24, the final product was further purified by re-crystallization of the final product in EtOH or CHCl$_2$. The species and the amounts of the reactants and the solvents for Examples 22 to 24 are shown in Table 6. The structure of each of the final products in Examples 22 to 24 was identified using NMR, MASS, and/or EA. The results are shown below.

Example 22

$^1$H-NMR (AMX 300 δ (D-CDCl$_3$)): 0.88 (t, 6H, J=6.5, 2×CH$_3$), 1.26-1.29 (m, 20H, 10×CH$_2$), 1.40-1.60 (m, 10H, 4×CH$_2$, 2×OH), 1.85-1.93 (m, 4H, 2×CH$_2$), 3.10-3.20 (m, 4H, 2×CH$_2$), 3.42 (t, 4H, J=7.7, 2×CH$_2$), 3.86-3.88 (m, 2H, 2×CH), 4.36-4.45 (m, 4H, 2×CH$_2$); LRMS calcd for C$_{29}$H$_{54}$N$_6$O$_2$ (M+H)$^+$: 519. Found: 519.

Example 23

$^1$H-NMR (AMX 300 δ (D-CDCl$_3$)): 0.88 (t, 6H, J=6.6, 2×CH$_3$), 1.28-1.30 (m, 12H, 6×CH$_2$), 1.46-1.60 (m, 10H, 4×CH$_2$, 2×OH), 1.85-1.93 (m, 4H, 2×CH$_2$), 3.10-3.18 (m, 4H, 2×CH$_2$), 3.42 (t, 4H, J=7.2, 2×CH$_2$), 3.86-3.89 (m, 2H, 2×CH), 4.38-4.45 (m, 4H, 2×CH$_2$); LRMS calcd for C$_{25}$H$_{46}$N$_6$O$_2$ (M+H)$^+$: 463. Found: 463.

Example 24

$^1$H-NMR (AMX 300 δ (D-CDCl$_3$)): 0.92 (t, 6H, J=7.2, 2×CH$_3$), 1.28-1.32 (m, 4H, 2×CH$_2$), 1.50-1.60 (m, 10H, 4×CH$_2$, 2×OH), 1.86-1.93 (m, 4H, 2×CH$_2$), 3.07-3.18 (m, 4H, 2×CH$_2$), 3.47 (t, 4H, J=7.5, 2×CH$_2$), 3.85-3.90 (m, 2H, 2×CH), 4.38-4.45 (m, 4H, 2×CH$_2$); LRMS calcd for C$_{21}$H$_{38}$N$_6$O$_2$ (M+H)$^+$: 407. Found: 407; Anal. calcd for C$_{21}$H$_{37}$N$_6$O$_2$: C 62.04%, H 9.42%, N 20.67%. Found: C 62.03%, H 9.52%, N 20.68%.

Example 25

Preparation of Triazine-Based Monomeric Compound Having the Following Formula (I-f)

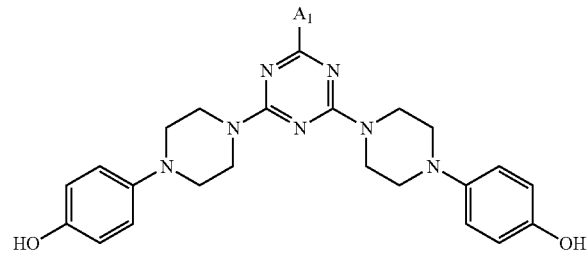

(I-f)

The steps for preparing the triazine-based monomeric compounds in Example 25, in which A$_1$ is —N(C$_8$H$_{17}$)$_2$, were similar to those for preparing the triazine-based monomeric compound of formula (I-d) except for the species and the amounts of the reactants and the solvents. The species and the amounts of the reactants and the solvents for Example 25 are shown in Table 6.

Structure Identification

The structure of the final product in Example 25 was identified using NMR and MASS. $^1$H-NMR (AMX 300 δ (D-CDCl$_3$)): 0.88 (t, 6H, J=6.9, 2×CH$_3$), 1.26-1.31 (m, 20H, 10×CH$_2$), 1.55-1.58 (m, 4H, 2×CH$_2$), 3.02-3.06 (m, 8H, 4×CH$_2$), 3.48 (t, 4H, J=7.8, 2×CH$_2$), 3.90-3.94 (m, 8H, 4×CH$_2$), 5.36 (s, 2H, 2×OH), 6.72 (d, 4H, J=9.0, 4×CH), 6.85 (d, 4H, J=9.0, 4×CH); LRMS calcd for C$_{39}$H$_{60}$N$_8$O$_2$ (M+H)$^+$: 673. Found: 673.

TABLE 6

| | Example | | | |
|---|---|---|---|---|
| | 22 | 23 | 24 | 25 |
| Mono-substituted cyanuric chloride g (mmol) | Prep. 1 0.78 g (2 mmol) | Prep. 2 3.33 g (10 mmol) | Prep. 3 2.77 g (10 mmol) | Prep. 1 3.50 g (9 mmol) |
| THF in step (1) (ml) | 10 | 20 | 20 | 20 |
| Solute in step (2) (g) | 4-piperidinol 0.51 g | 4-piperidinol 2.53 g | 4-piperidinol 2.53 g | 1-(4-hydrophenyl)piperazine 2.34 g |
| THF in step (2) (ml) | 20 | 20 | 20 | 10 |
| Triethylamine in step (3) (g) | 0.81 g | 2.24 g | 2.24 g | 2.24 g |
| Solvent used to dissolve the reaction mixture after removing THF | Ethyl acetate | CH$_2$Cl$_2$ | Ethyl acetate | CH$_2$Cl$_2$ |
| Solvent used to purification after removing MgSO$_4$ | EtOH | CH$_2$Cl$_2$ | EtOH | EtOH |
| Final product (g) | 0.79 | 4.16 | 3.74 | 1.74 |
| Yield (%) | 75 | 90 | 92 | 32 |

Experiment
Preparation of Degradable Polymer Having the Following Formula (III)

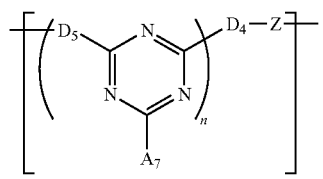

Preparation Steps:

(1) To a mixture solution containing N-methyl-pyrrolidone and anhydrous dichloromethane, 1 mmol of the triazine-based monomeric compounds obtained in each of Examples 1 to 4 was added to give a reaction solution. The reaction solution was heated to 40° C. to dissolve the triazine-based monomeric compound.

(2) After the triazine-based monomeric compound was completely dissolved in the reaction solution, 1 mmol of MDI was added thereto to form a reaction mixture. The reaction mixture was allowed to react at room temperature for 12 hours.

(3) The reaction mixture was slowly added into methanol, followed by stirring at 50° C. for 24 hours.

(4) The product was obtained by filtration and the product was allowed to stand overnight to evaporate methanol.

Experiments 1 to 8

The degradable polymers in Experiments 1 to 8 were prepared using the aforesaid preparation steps. The species of the triazine-based monomeric compound and diisocyanate, the amount of N-methyl-pyrrolidone and anhydrous dichloromethane in the mixture solution, and the weight of the product for Experiments 1 to 8 are shown in Table 7.

TABLE 7

| Exp. | Triazine-based monomeric compound | Diisocyanate | N-methyl-pyrrolidone (ml) | $CH_2Cl_2$ (ml) | Product (g) |
|---|---|---|---|---|---|
| 1 | Example 1 | MDI | 1 | 4 | 1.0842 |
| 2 | Example 2 | MDI | 2 | 5 | 0.978 |
| 3 | Example 3 | MDI | 3 | 7 | 0.871 |
| 4 | Example 4 | MDI | 3 | 7 | 0.962 |
| 5 | Example 1 | PDI | 1 | 4 | 0.995 |
| 6 | Example 2 | PDI | 2 | 6 | 0.892 |
| 7 | Example 3 | PDI | 3 | 8 | 0.786 |
| 8 | Example 4 | PDI | 2 | 8 | 0.877 |

Structure Identification

The structure of the degradable polymers in Experiments 1 to 8 was identified using FT-IR. The FT-IR results show that no intensity was detected for the N=C=O absorbance peak at 2270 cm$^{-1}$, C=O absorbance peak for urea group was observed at 1650 cm$^{-1}$, and N—H absorbance peak for urea group was observed at 3450 cm$^{-1}$. This reveals that the triazine-based monomeric compound of this invention is reacted with diisocyanate to produce the polymer of formula (III) of this invention.

Measurement of $M_n$ and $M_w$

Number average molecular weight ($M_n$) and weight average molecular weight ($M_w$) for each of the polymers of Experiments 1 to 8 were determined by gel permeation chromatography, in which DMF was used as a solvent. The polydispersity index was measured using the following formula:

$$\text{Polydispersity index} = M_w/M_n$$

The results are shown in Table 8.

TABLE 8

| Experiment | $M_w$ | $M_n$ | Polydispersity index |
|---|---|---|---|
| 1 | 105432 | 51671 | 2.04 |
| 2 | 124806 | 50123 | 2.49 |
| 3 | 105463 | 49747 | 2.12 |
| 4 | 93612 | 41058 | 2.28 |
| 5 | 97360 | 40099 | 2.42 |
| 6 | 89885 | 38911 | 2.31 |
| 7 | 64061 | 32852 | 1.95 |
| 8 | 75288 | 32877 | 2.29 |

Solubility Test

Each of the degradable polymers in Experiments 1 to 8 was dissolved in NMP, DMAC, DMF, DMSO, and THF. The results are shown in Table 9. The results show that the degradable polymers of this invention have a good solubility in the aforesaid solvents. In particular, the polymers made from MDI have superior solubility over those made from PDI.

TABLE 9

| Experiment | NMP | DMAC | DMF | DMSO | THF |
|---|---|---|---|---|---|
| 1 | ++ | ++ | + | + | ++ |
| 2 | ++ | ++ | ++ | + | +− |
| 3 | ++ | ++ | ++ | + | ++ |
| 4 | ++ | ++ | + | +− | − |
| 5 | + | ++ | ++ | + | ++ |
| 6 | ++ | ++ | ++ | +− | +− |
| 7 | ++ | ++ | ++ | +− | − |
| 8 | ++ | ++ | + | +− | − |

++: soluble at room temperature
+: soluble at 50-80° C.
+−: partly soluble or swelling
−: insoluble Heat Property and Water Absorption Tests Softening temperature (Ts) for each of the polymers of Experiments 1 to 8 was measured using TMA. Weight loss upon heating, heat decomposition temperature (Td), char yield, and water absorption for each of the polymers were measured using TGA. The results of Ts, $T_{10\%}$, Td, and char yield are shown in Table 10, in which $T_{10\%}$ indicates, in nitrogen atmosphere, the temperature at which the weight of the polymer reduces 10% upon heating. The results show that $T_{10\%}$ for each of the polymers of Experiments 1 to 8 is about 350° C. and exhibits good thermal stability. In addition, the polymers of Experiments 1, 2, 5, and 6 were stored under air at room temperature for half a year and then investigated by TGA instrument to study their water absorption. The results show that no weight change for the polymers from Experiments 1, 2, 5, and 6 was found below 150° C. under nitrogen atmosphere, indicating these polymers does not absorb moisture under air at room temperature.

TABLE 10

| Exp. | $T_{10\%}$ (° C.) | $T_s$ (° C.) | $T_d$ (° C.) | Char yield (%) |
|---|---|---|---|---|
| 1 | 361.53 | 116.76 | 327 | 14.26 |
| 2 | 358.01 | 158.00 | 340 | 15.62 |
| 3 | 365.72 | 171.97 | 340 | 15.46 |

TABLE 10-continued

| Exp. | $T_{10\%}$ (° C.) | $T_s$ (° C.) | $T_d$ (° C.) | Char yield (%) |
|---|---|---|---|---|
| 4 | 357.72 | 167.69 | 344 | 24.57 |
| 5 | 357.00 | 131.10 | 316 | 7.32 |
| 6 | 335.29 | 142.49 | 319 | 10.23 |
| 7 | 345.37 | 164.54 | 341 | 11.32 |
| 8 | 355.87 | 170.33 | 340 | 11.81 |

Acid Decomposition Test 2 mg of each of the degradable polymers in Experiments 1 to 8 was disposed in several HCl solutions diluted with THF and having pH values of 1, 2, 3, and 4, respectively. The decomposition was monitored using TLC. The results reveal that decomposition of each of the polymers of this invention was observed after 24 hours in pH 4, after 20 minutes in pH 3, and after 1 to 2 minutes in pH 1-2. The decomposition rate for each of the polymers becomes higher and higher.

Cell Viability Test—MTT Assay

The degradable polymers in Experiments 2 and 3 were further conducted cell viability test by MTT assay using Cline 9 cells (commercially available from the Biosource Collection and Research Center (BCRC) of the Food Industry Research and Development Institute (FIRDI), CRL-1439) and hepatic satellite cells (HSC, available from Taichung Veterans General Hospital).

The degradable polymers in Experiments 2 and 3 were dissolved in 2 mg/cc of DMF to give first and second solutions. Each of the first and second solutions was dropped on a 15 mm$^2$ cover glass, followed by removing DMF in a vacuum oven to give sample 1 and sample 2. After sterilizing by UV radiation, samples 1 and 2 and a cover glass without the degradable polymers (used as a control 2) were disposed in wells of a 24-well plate. Subsequently, 1 ml of 2.5×10$^4$ cells/ml of Clone 9 cell suspension in a MEM medium (containing 10% FBS, 1.5 g/L of sodium bicarbonate, 0.1 mM non-essential amino acid, and 1.0 mM sodium pyruvate) was added into each of a blank well (used as control 1) and the wells containing sample 1, sample 2, and control 2. The plate was then cultivated in an incubator (37° C., 5% CO2) for a period of 48 hours. 1 ml of 3-(4,5-dimethyl-2-thiazolyl)-2,5-diphenyl-2H-tetrazolium bromide (MTT, 0.5 mg/ml) was added into each well and reacted for 3 hours, followed by removal of the supernatant and addition of 1 ml of 2-propanol. Thereafter, the absorbance at 570 nm was read for each well using Benchmark Plus (Bio-Rad). This experiment was repeated three times for each group. The higher the absorbance, the more the cell number is. The results are shown in Table 11.

The degradable polymers in Experiments 2 and 3 were conducted MTT assay again based on the aforesaid method except that HSC cell was used to replace Clone 9 cell. The absorbance for each well (i.e., sample 3, sample 4, control 3, and control 4) is shown in Table 11.

TABLE 11

| Group | Absorbance | B % | G % |
|---|---|---|---|
| Control 1 | 0.112 | 100 | — |
| Control 2 | 0.113 | 100.89 | 100 |
| Sample 1 | 0.098 | 87.24 | 86.47 |
| Sample 2 | 0.096 | 85.46 | 84.71 |
| Control 3 | 0.155 | 100 | — |
| Control 4 | 0.152 | 98.06 | 100 |
| Sample 3 | 0.151 | 97.41 | 99.34 |
| Sample 4 | 0.132 | 85.56 | 87.25 |

B %: Percentage of absorbance based on the absorbance of control 1 or control 3
G %: Percentage of absorbance based on the absorbance of control 2 or control 4

It is evident from Table 11 that, Clone 9 cells and HSC cells can still grow in the presence of the degradable polymers of this invention. This reveals that the degradable polymers of this invention have no cell toxicity and suggests that the degradable polymers of this invention could probably by used in the biochemical or medical field.

Transparency Test for a Film Made from the Degradable Polymer of this Invention 0.5-1 g of each of the degradable polymers in Experiments 1 to 8 was dissolved in 10 ml of THF to form a polymer solution. Each of the polymer solutions was placed in a dish with a diameter of 5.5 cm, followed by drying in an oven at 50° C., thereby giving films having thicknesses of 0.073 mm, 0.068 mm, 0.098 mm, 0.132 mm, 0.087 mm, 0.048 mm, 0.193 mm, and 0.085 mm, respectively. Transparency for each of the films was measured using UV-visible light spectrometer. The cutoff wavelength for the degradable polymers in Experiments 1 to 8 ranges from 350 nm to 380 nm. The results show that the films made from the degradable polymers of this invention have good transparency.

According to the present invention, the polymer prepared from the triazine-based monomeric compound of this invention can be degraded at a low pH value and therefore can be friendly to the global environment. Moreover, the polymer thus obtained exhibits good physical properties (e.g., solubility, heat stability, water absorption, etc.) and cell compatibility.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

What is claimed is:

1. A degradable polymer prepared by:
reacting a triazine-based monomeric compound with a monomer or a prepolymer which is capable of reacting with the triazine-based monomeric compound by condensation or addition polymerization, wherein the triazine-based monomeric compound is represented by the following formula (I):

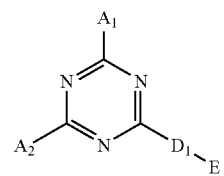

wherein E is H or a substituted triazine group represented by the following formula:

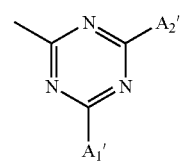

and D$_1$ is represented by the following formula:

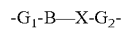

-G$_1$-B—X-G$_2$- wherein B is selected from the group consisting of 1,3-cyclohexylene, 1,4-cyclohexylene, meta-phenylene, para-phenylene, and a divalent heterocyclic group;

wherein, when B is 1,3-cyclohexylene, 1,4-cyclohexylene, meta-phenylene, or para-phenylene and X is a hydrocarbylene group or a single bond, $G_1$ and $G_2$ are independently N or O; and wherein, when B is a divalent heterocyclic group and X is a hydrocarbylene group or a single bond, $G_1$ and $G_2$ are independently N, O, or a single bond, in which, when one of $G_1$ and $G_2$ is a single bond, an atom of said heterocyclic ring bonding to said single bond is a heteroatom, and in which, when $G_2$ is a single bond, X is a single bond, and when E is H, B is a 1,4-piperazinylene group, 1,4-piperidylene group or

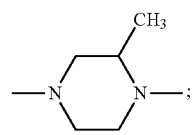

wherein each of $A_1$ and $A_2$ is independently a substituent group, and at least one of $A_1$ and $A_2$ is an active hydrogen-containing group for condensation or addition reaction; and wherein each of $A_1'$ and $A_2'$ is independently a substituent group, and at least one of $A_1'$, and $A_2'$, is an active hydrogen-containing group for condensation or addition reaction.

2. The degradable polymer as claimed in claim 1, wherein said degradable polymer is represented by the following formula (III):

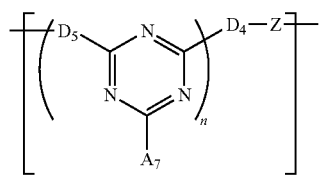

wherein $D_4$ and $D_5$ has the same definition as $D_1$ in claim 1, and $D_4$ and $D_5$ in each occurrence can be independently the same or different, wherein Z is a divalent group represented by the following formula (V):

$$-R_1-Y-R_2- \quad (V)$$

wherein Y is a hydrocarbylene group, and $R_1$ and $R_2$ in each occurrence are independently a bridging group of —CO— or —CO—NH—, so as to form a linkage of
—O—CO—,
—O—CO—NH—,
or

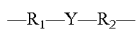

with $D_4$ and $D_5$, respectively;
wherein $A_7$ is a substituent group; and
wherein n is an integer ranging from 1 to 2.

3. The degradable polymer as claimed in claim 2, wherein $D_4$ and $D_5$ in each occurrence are independently

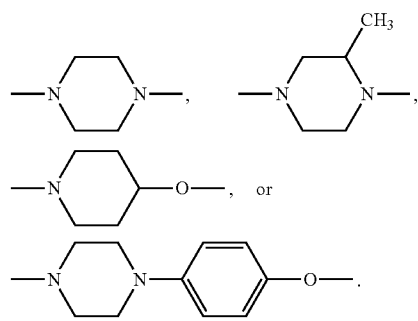

4. The degradable polymer as claimed in claim 2, wherein $A_7$ is a substituted amino group.

5. The degradable polymer as claimed in claim 4, wherein $A_7$ in each occurrence is a dibutylamino group, a dihexylamino group, a dioctylamino group, a piperidino group, a morpholinyl group, a diphenylamino group,

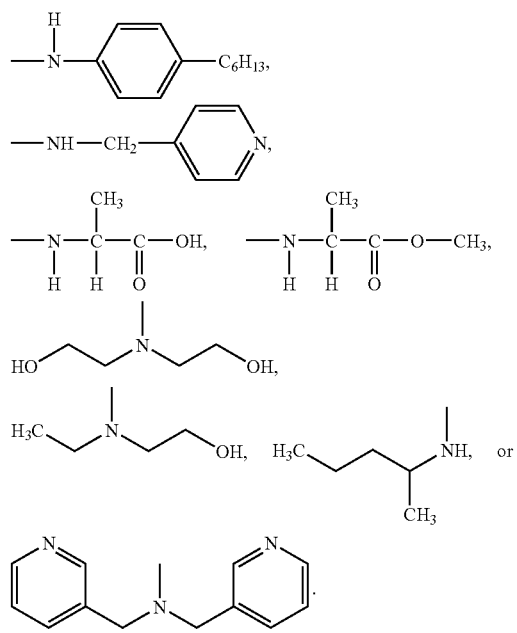

6. The degradable polymer as claimed in claim 2, wherein Y is an aromatic group.

7. The degradable polymer as claimed in claim 6, wherein Y in each occurrence is

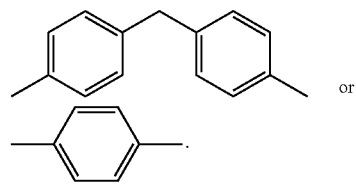

8. The degradable polymer as claimed in claim 1, wherein B is a 1,4-piperazinylene group, a 1,4-piperidylene group, 1,3-cyclohexylene, 1,4-cyclohexylene, meta-phenylene, para-phenylene, or

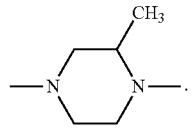

9. The degradable polymer as claimed in claim 8, wherein E is a substituted triazine group, $G_1$, $G_2$, and X are single bonds, and B is a 1,4-piperazinylene group.

10. The degradable polymer as claimed in claim 8, wherein E is H, $G_1$ is a single bond, $G_2$ is a single bond or O, B is a 1,4-piperazinylene group or a 1,4-piperidylene group, and X is a single bond or a phenyl group.

11. The degradable polymer as claimed in claim 1, wherein each of $A_2$ and $A_2'$ is independently said active hydrogen-containing group, said active hydrogen-containing group being a substituted or non-substituted piperazino group, a hydroxyl piperidino group, or a hydroxyphenyl piperazino group.

12. The degradable polymer as claimed in claim 11, wherein each of $A_1$ and $A_1'$ is independently a substituted amino group.

13. The degradable polymer as claimed in claim 12, wherein said substituted amino group is a dibutylamino group, a dihexylamino group, a dioctylamino group, a piperidino group, a morpholinyl group, a diphenylamino group,

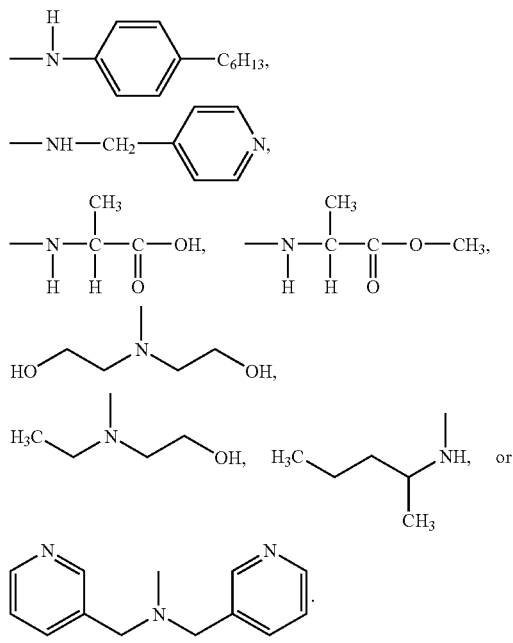

14. The degradable polymer as claimed in claim 1, wherein E is a substituted triazine group; $G_1$, $G_2$, and X are single bonds; B is a 1,4-piperazinylene group; each of $A_1$ and $A_1'$ is —N(C$_4$H$_9$)$_2$, —N(C$_6$H$_{13}$)$_2$, —N(C$_8$H$_{17}$)$_2$, or

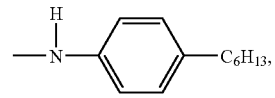

and each of $A_2$ and $A_2'$ is a piperazino group optionally substituted with a methyl group, a hydroxyl piperidino group, or a hydroxyphenyl piperazino group.

15. The degradable polymer as claimed in claim 1, wherein E is H; $A_1$ is a dibutylamino group, a dihexylamino group, a dioctylamino group, a piperidino group, a morpholinyl group, a diphenylamino group, or

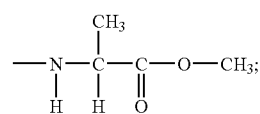

$A_2$ is $D_2H$; and $D_1$ and $D_2$ are independently

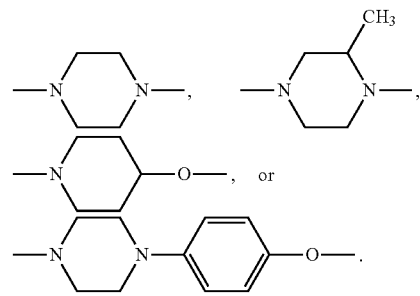

16. The degradable polymer as claimed in claim 1, wherein said triazine-based monomeric compound is prepared from a di-triazine compound, said di-triazine compound being represented by the following formula (II):

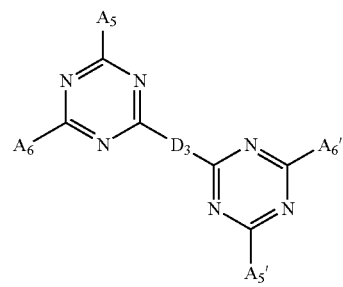

wherein $D_3$ has the same definition as $D_1$ in claim 1, $A_6$ and $A_6'$ are halogen, and $A_5$ and $A_5'$ are independently halogen or a substituent group.

17. The degradable polymer as claimed in claim 16, wherein $D_3$ is a 1,4-piperazinylene group; and $A_5$, $A_5'$, $A_6$, and $A_6'$ are Cl.

18. The degradable polymer as claimed in claim 16, wherein each of $A_5$ and $A_5'$ is independently a substituted amino group, said substituted amino group is a dibutylamino group, a dihexylamino group, a dioctylamino group, a piperidino group, a morpholinyl group, a diphenylamino group,

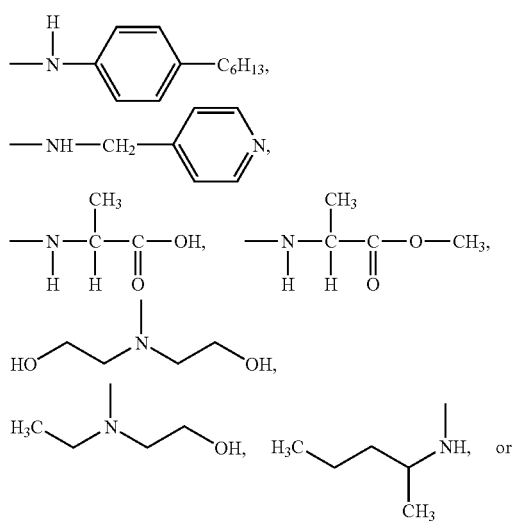
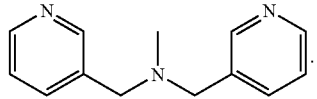
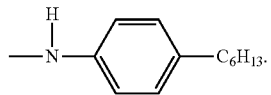
19. The degradable polymer as claimed in claim 16, wherein $D_3$ is a 1,4-piperazinylene group; $A_6$ and $A_6'$ are Cl; and $A_5$ and $A_5'$ are independently —N(C$_4$H$_9$)$_2$, —N(C$_6$H$_{13}$)$_2$, —N(C$_8$H$_{17}$)$_2$, or
* * * * *